May 4, 1976
R. S. MOORE
MINIATURE ROSE PLANT
Filed Dec. 9, 1974
Plant Pat. 3,876
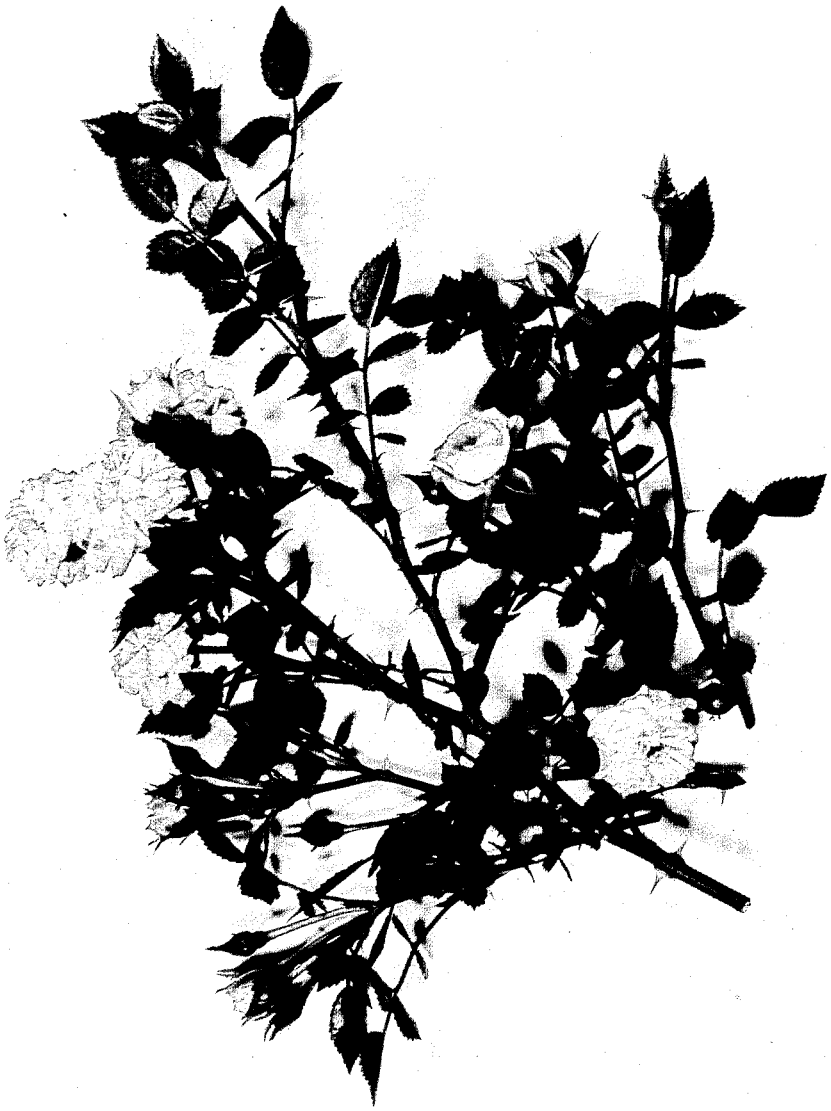

United States Patent

Plant Pat. 3,876

Patented May 4, 1976

3,876

MINIATURE ROSE PLANT

Ralph S. Moore, 2519 E. Noble Ave.,
Visalia, Calif. 93277

Filed Dec. 9, 1974, Ser. No. 530,724
Int. Cl. A01h 5/00
U.S. Cl. Plt.—7 1 Claim

The present invention relates to a new and distinct variety of hardy, dwarf, bush type rose plant of the miniature class; the variety being primarily characterized—as to novelty-by bright orange-pink buds and flowers which in general color effect are orange-pink similar in color to "Margo Koster" (*polyantha*, not patented) but softer shade.

The variety is further characterized by:

An abundance of bloom, with flowers borne singly or several to the stem in sprays or clusters.

Little fragrance.

A plant which is vigorous, of rounded spreading shape and with glossy, moderately small foliage with pointed leaflets; the buds and flowers being similar in form, but smaller in size, to the variety "Cri Cri" (miniature—not patented). The plant, which has a normal height of 12 to 16 inches can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, Calif., under conditions of careful control and observation, as a cross between an un-named seedling (*R. wichuriana* × Floradora, not patented) as the seed parent and "Fire Princess" (miniature—Plant Pat. 3,084) as the pollen parent.

Subsequent to origination of the variety I successfully asexually reproduced it, in my nursery located as aforesaid, by budding as well as by cuttings; the reproductions having run true in all respects.

The color photograph illustrates the variety, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bush; seedling; greenhouse; outdoors; cut flowers garden decoration; potted plant.

Class: Miniature.

Flowers: Continuity: Continuous—repeat bloom all season.

Fragrance: Very little.

Flowers borne: Singly and several together (3 to 5, sometimes more) on strong, medium length stems.

Quantity of bloom: Abundant both outside and in greenhouse.

Bud: Peduncle—medium length; slender but sturdy; erect; medium green, sometimes tinted bronze; hairs—few to none. Before calyx breaks; size—small. Form: short; pointed; with a few foliaceous appendages and few or no hairs on surface of bud; with foliaceous parts extending beyond the tip of the bud equal to one half or less of its length. Color—medium green, occasionally tinted with bronze. As calyx breaks: color—medium orange-red (Vermilion 18/1). As first petal opens: same general color (Vermilion 18 to Vermilion 18/1) but showing small yellow area near base of petal; size: small.

Bloom: Size when fully open—small, averaging about

1¼" (3.2 cm.). Petallage—double, 50–60 (with, sometimes, several small petals rolled around pistils) arranged fairly regularly. Form—full, slightly cupped to flat at first, becoming more rounded in the center, with petals rolled loosely outward, and later at maturity, full with higher center with petals rolled loosely outward and downward.

Petals: Fairly thick; satiny both inside and outside. Shape—Outside petals, broad lanceolate with acute tip; inside—lanceolate with acute tip.

Color: Newly opened flower from a plant grown in cool plastic greenhouse (November 1974), Visalia, Calif.

*Outside petal:* Outside surface—Near Mandarin Red 17/2 or Azalea Pink 618/1 with small whitish area at base; inside surface—Near Mandarin Red 17/2 or Azalea Pink 618/1 with small yellowish area at base.

*Intermediate petal:* Outside surface—Near Mandarin Red 17/2 or Azalea Pink 618/1 with small whitish area at base; inside surface—Near Mandarin Red 17/2 or Azalea Pink 618/1 with small yellowish area at base.

*Inner petal:* Outside surface—same as intermediate petal; inside surface—same as intermediate petal. General color effect newly opened flowers—bright orange-pink color, similar to "Cri Cri" but brighter. Three days open—similar color but less intense.

Behavior—As flowers age petals become lighter (more pink) shade before dropping off. Spent petals usually drop off (may hang on in cool, damp weather).

Flower longevity (September 1974)—Bush in garden or pot, 5 to 7 days or longer. Cut flowers at living room temperature, 4 to 6 days.

Reproductive organs:

Stamens: Few to none.
Filaments: Short; yellow.
Anthers: Yellow.
Pollen: Little or none.
Pistils: Average number, often imperfect.
Styles: Fairly even; short; bunched; color—greenish.
Stigma: Nearly white or pale yellow-green.
Ovaries: All enclosed in calyx.
Hips: None.
Sepals: Permanent; spear shaped.
Seeds: None.

Foliage:

Leaves—Compound of five leaflets, sometimes seven; abundant; moderately small; leathery, glossy.

Leaflets—

Shape: Lanceolate; apex acute; base rounded.
Color: Normal green; new growth—reddish or tinted bronze.
Rachis: Medium strength; upper side has several tiny short prickles, grooved; under side moderately thorny with few very tiny prickles.
Stipules: Medium long; medium width; medium length narrow points which may turn out at both more or less than 45 degrees.

Growth:

Habit: Dwarf; bushy; rounded; much branched.
Growth: Free; vigorous.
Canes: Medium; slender, sturdy.
Main Stems: Color: Medium green (may darken with age). Thorns: Average number; medium to long; hooked slightly downward; color: brown. Prickles—none. Hairs—none.
Branches: Color: Medium green. Thorns: average thorny. Medium length; slender; inclined slightly downward. Medium to short oval base. Prickles—none. Hairs—none.

New shoots: Color: Often tinted red or bronze. Thorns: Average number; medium length; nearly straight, hooked slightly downward, reddish color; sharp points; base oval. Prickles—none. Hairs—none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, relatively dwarf, rounded, much branched, bush type, as illustrated and described, characterized by buds and flowers resembling the "Cri Cri" (not patented) miniature rose in general form, the color being a bright shade of orange pink, the general color effect being a bright orange pink, resembling the color of Margo Koster (*polyantha*—not patented); and further characterized by a plant which is of vigorous, relatively compact habit, easy to propagate from cuttings; with small glossy foliage, often tinted reddish or bronze on new growth; with flowers borne singly or several to the stem in spray or cluster.

No references cited.

ROBERT E. BAGWILL, Primary Examiner